United States Patent [19]
Fontenot et al.

[11] Patent Number: 5,344,436
[45] Date of Patent: * Sep. 6, 1994

[54] LOCALIZED HEAT TRANSFER DEVICE

[75] Inventors: Mark G. Fontenot, New Orleans, La.; Thomas G. Miller, Houston, Tex.

[73] Assignee: Lake Shore Medical Development Partners, Ltd., Houston, Tex.

[*] Notice: The portion of the term of this patent subsequent to Dec. 29, 2009 has been disclaimed.

[21] Appl. No.: 852,431

[22] Filed: Mar. 16, 1992

Related U.S. Application Data

[63] Continuation-in-part of Ser. No. 462,495, Jan. 8, 1990, Pat. No. 5,174,285.

[51] Int. Cl.$^5$ .............................................. A61F 7/00
[52] U.S. Cl. ................................... 607/104; 165/46
[58] Field of Search ............... 165/46; 128/399–403, 128/379, 380; 604/153; 62/259.3; 416/179, 180, 184; 222/61

[56] References Cited

U.S. PATENT DOCUMENTS

| | | | |
|---|---|---|---|
| 1,025,012 | 4/1912 | Norwood | 128/403 |
| 2,566,865 | 9/1951 | Whgerter | 165/46 |
| 3,046,903 | 7/1962 | Jones | 604/153 |
| 3,074,410 | 1/1963 | Foster | 128/400 |
| 3,088,288 | 5/1963 | Elfving | 62/3 |
| 3,154,926 | 11/1964 | Hirschhorn | 62/3 |
| 3,480,015 | 11/1969 | Gonzalez | 128/276 |
| 3,738,372 | 6/1973 | Shioshvili | 128/400 |
| 3,867,939 | 2/1976 | Moore et al. | 128/254 |
| 3,967,627 | 7/1976 | Brown | 128/400 |
| 4,114,620 | 9/1978 | Moore et al. | 128/254 |
| 4,199,307 | 4/1980 | Jassawalla | 604/153 |
| 4,256,437 | 3/1981 | Brown | 604/153 |
| 4,259,961 | 4/1981 | Hood, III | 128/400 |
| 4,335,726 | 6/1982 | Kolstedt | 128/400 |
| 4,459,468 | 7/1984 | Bailey | 219/490 |
| 4,476,685 | 10/1984 | Aid | 62/3 |
| 4,523,594 | 6/1985 | Kuznetz | 128/402 |
| 4,691,761 | 9/1987 | Elkins et al. | 165/46 |
| 4,691,762 | 9/1987 | Elkins | 128/400 |
| 4,844,072 | 7/1989 | French et al. | 128/400 |
| 4,930,317 | 5/1988 | Klein | 62/3.3 |
| 4,962,761 | 10/1990 | Golden | 128/403 |
| 5,002,201 | 3/1991 | Hancock et al. | 222/61 |
| 5,174,285 | 12/1992 | Fontenot | 607/104 |

FOREIGN PATENT DOCUMENTS

| | | |
|---|---|---|
| 746650 | 8/1944 | Fed. Rep. of Germany . |
| 1053537 | 3/1959 | Fed. Rep. of Germany . |
| 2435678 | 9/1978 | France . |
| 2417974 | 11/1979 | France . |
| WO/8606964 | 12/1986 | World Int. Prop. O. . |

OTHER PUBLICATIONS

Publication from ECRI, vol. 17(11), Nov. 1988.
Publication from Marlow Industries, Inc.
Health Devices Sourcebook, 1981–1982 Reference: Hypo/Hperthermia Blankets, Sep. 1981.
Advertising brochures from Seabrook, Medical Systems, Inc.
Advertising brochure from American Hospital Supply.
Advertising brochure from American Medical Systems.
Advertising brochure from Thermotemp, Inc.
Advertising brochure from Kendall Healthcare Products Co.
Advertising brochure from Cincinnati SubZero.
Advertising brochures from Gaymar Industries.
Electri-Cool Localized Cold Therapy Unit Product Manual by Seabrook Medical Systems, Inc., Apr. 25, 1991.
Advertisment by Melcor, Materials Electronic Products Corp.
Advertisement by March Mfg., Inc.
Advertisement brochure by Lambda Electronics, Inc.
Advertisement brochure by PMI Motion Technologies.
Advertisement by Marlow Industries, Inc.
Advertisement by Comair Rotron Co.

*Primary Examiner*—Mark S. Graham
*Attorney, Agent, or Firm*—Arnold, White & Durkee

[57] ABSTRACT

The invention provides systems for topically heating or cooling an animal or human body, and more particularly concerns a modular system in which a heating or cooling liquid is circulated in a hermetically sealed flow path between a heating or cooling device and a heating or cooling pad. In a preferred embodiment, the flow path includes a cassette which is reversibly engageable with a pump and a heating or cooling unit located in a housing.

38 Claims, 8 Drawing Sheets

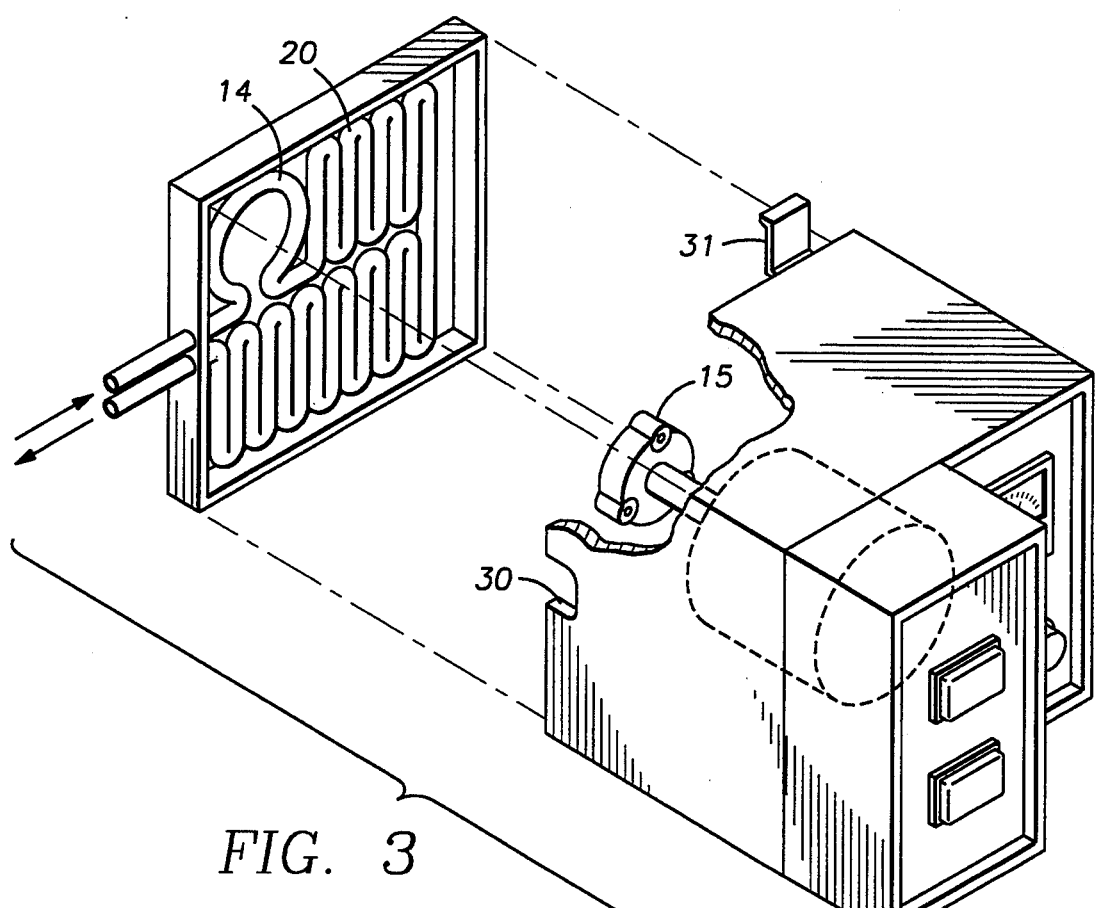
FIG. 3
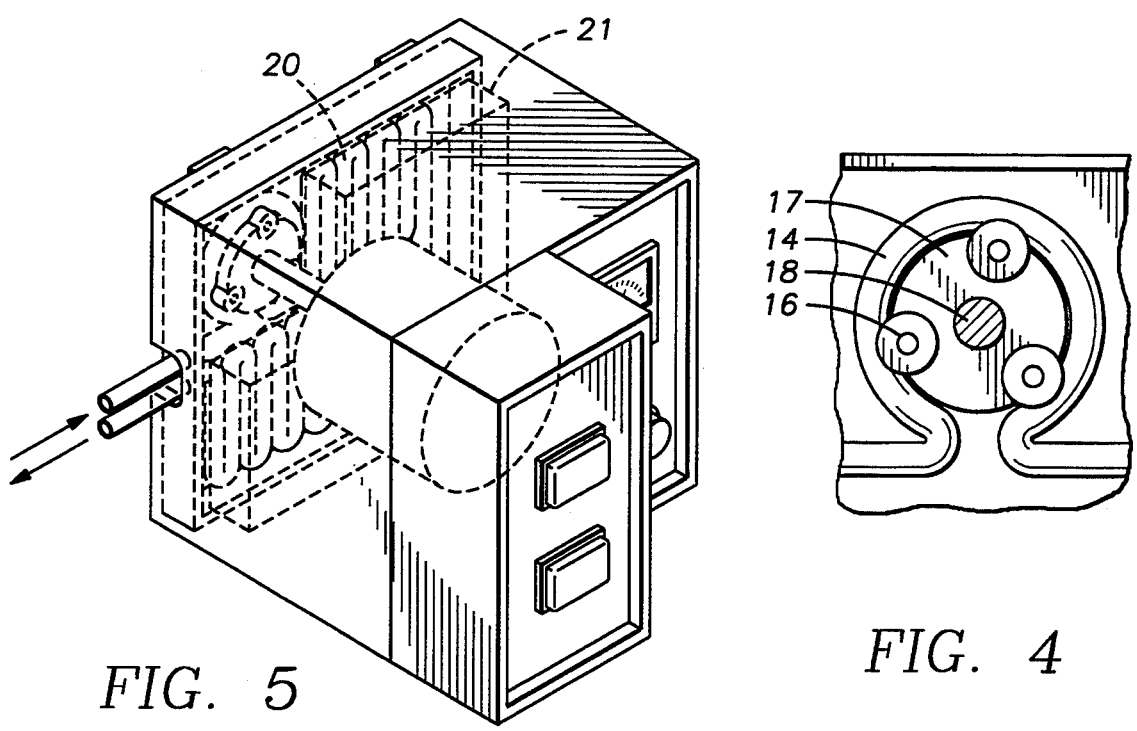
FIG. 5
FIG. 4

LOCALIZED HEAT TRANSFER DEVICE

This application is a continuation-in-part of application No. 07/462,495 filed on Jan. 8, 1990, now U.S. Pat. No. 5,174,285.

BACKGROUND OF THE INVENTION

A. Field of the Invention

The present invention relates to systems for topically heating or cooling an animal or human body. The invention more particularly concerns such a system in which a heating or cooling liquid is circulated in a hermetically sealed flow path between a heating or cooling device and a heating or cooling pad. In an especially preferred form, the flow path includes a cassette or similar cartridge which is engageable with a pump and a heating or cooling unit. The flow path is permanently sealable and precludes a need for joints, couplings or similar fluid connectors for assembling and disassembling the flow path.

B. The Prior Art

Localized hyperthermia or hypothermia (topical application of heat or cold, respectively, to selected regions of the body) is used to treat a wide variety of medical/surgical conditions in hospitals, nursing homes, and other care giving locations and is becoming increasingly important in areas such as home health care and sports medicine. Thrombophlebitis, cellulitis, decubitus ulcerations, incisional pain and swelling, post-partum and post-operative pain and swelling, muscle pathology and pain, and joint pathology and pain are some common medical/surgical conditions for which localized hypothermia or hyperthermia can be an effective adjunctive therapy.

Techniques that deliver localized hypothermia or hyperthermia can be classified as moist or dry. With the moist technique, a hydrated surface is in direct or indirect contact with the body; with the dry technique, a dry surface is in direct or indirect contact with the body. Devices that deliver localized hypothermia or hyperthermia can be characterized as continuous or intermittent. They may be referred to generically as thermiatric devices or units. Continuous devices draw their energy from various types of electrical power sources. Intermittent devices typically draw their energy from anything buy electrical power sources, i.e., exothermic/endothermic and chemical systems.

Localized, heat transfer devices known to those of skill in the art include simple devices, such as hot-water bottles and ice packs, as well as somewhat more sophisticated electromechanical systems.

One commercially available single use system comprises an enclosed rupturable membrane separating two or more chemicals. The application of pressure to the membrane causes it to rupture, allowing the chemicals to mix in an endothermic or exothermic reaction. The net effect is a bag that absorbs heat from or adds heat to the body. Although this system can be effective and practical when localized short-term cooling or heating of the body is desired, it is not reusable and does not deliver constant uniform controlled heating and cooling.

The electrical heat lamp is another system used to add heat to a specific region of the body. Although many commercially available heat lamps have electrical systems that allow one to control the intensity of the light bulb and thereby control temperature, those systems are cumbersome and do not deliver uniform or site specific controlled heating.

More complicated systems require assembly and comprise a flexible polymeric applicator pad which has an inlet port and an outlet port. The ports must be reversibly connected, through a series of individual tubes, to a central fluid reservoir located in a separate housing. With these systems, the housing will contain a mechanism for heating or cooling the fluid in the reservoir and for circulating the fluid through the reservoir and into the applicator pad. For example, U.S. Pat. No. 4,459,468 describes an electromechanical controlled-temperature fluid circulating system designed for assembly to and use in reversible combination with a flexible thermal blanket or pad. This type of system comprises a fluid reservoir, heat transfer elements, temperature control circuitry, power supply, pump, and inlet and outlet ports reversibly connected to two flexible tubes that, in turn, connect the system to the pad. The reservoir contains a fluid, usually water, that can be heated or cooled by the heat transfer elements disposed within or adjacent the reservoir. The temperature of the fluid is monitored by the temperature control circuitry, which, in turn, is electrically connected to thermal modules that can be activated to maintain a desired fluid temperature. A pump is connected between the reservoir and the inlet and outlet ports. The inlet and outlet ports much be connected to two tubes for transferring fluid to an additional set of ports, disposed in the separate flexible applicator pad. The system must be reversibly assembled prior to use by coupling the pad to the two tubes, which are in turn connected to the ports in the housing containing the reservoir and pump.

A system described in U.S. Pat. No. 3,967,627 also has a fluid reservoir or standpipe, which is vented to the atmosphere, a heat exchanger with control circuitry, a peristaltic pump, and inlet and outlet ports. With this system, the heat transfer fluid is stored and maintained in the vented reservoir, and a peristaltic pump is used to force the fluid to flow through a heat exchanger, where the fluid temperature is sensed and regulated, to the outlet port. For assembly, the latter may be reversibly connected to a tube which may be reversibly connected to yet an additional port located in the applicator pad. As with the device set forth in U.S. Pat. No. 4,459,468, the system must be reversibly assembled prior to use by coupling the pad to conduits, which are in turn connected to the ports in the housing.

It can readily be seen that with devices of the types described above, the applicator pad is initially fluidless and, when the pad is not is use, the inlet and outlet ports are open to the atmosphere, preventing maintenance of sterile conditions within the pad. When one desires to use the pad, the ports must be reversibly coupled to a pair of intermediate conduits. The conduits are, in turn, reversibly connected to another pair of ports mounted on the housing.

Such systems are inefficient, messy, and in some cases hazardous to use. First, the reversible coupling of the applicator pad to the fluid circulating system is cumbersome and time consuming. The devices have multiple fluid couplings, which must be manually connected and often leak, thereby preventing one from maintaining the circulating fluid as sterile. Inexactly fitted connections result in fluid leakage at the couplings, for example, between the inlet and outlet ports of the applicator pad and the intermediate tubing and between the tubing and the ports leading to the fluid reservoir. Additionally, when the system is disassembled after use, additional fluid leaks from the applicator pad and the intermediate tubing that connects the fluid circulating system to the applicator pad. This leakage increases the potential for electrical shock and spread of disease, particularly nosocomial infections, as contaminated fluid leaks onto the patient's bed or body parts to which the pad is applied, often a recent surgical wound. It also reduces the volume of fluid in the reservoir and, in conjunction with the venting, necessitates frequent refilling of the fluid reservoir.

Second, the efficiency of systems having vented reservoirs and orientation dependent pumps is contingent on the proper placement of the fluid circulating system relative to the applicator pad. If the elevation of the fluid circulating system is the same as that of the applicator pad, the systems may function normally. However, as the difference between the elevation of the fluid circulating system and the elevation of the applicator pad increases, the efficiency of the system decreases. Moreover, because the reservoirs are vented, any tilting of the fluid circulating system may cause fluid to leak or spill. Fluid can also evaporate from the vented reservoir; hence, the fluid level requires constant monitoring in order to allow one to maintain the proper level of circulating fluid for safe operation of the unit. Finally, the vent facilitates contamination of fluid in the reservoir.

Finally, non-sterility of fluids in the reservoir and the difficulty or impossibility of cleaning or sterilizing reusable parts of the device may induce the spread of nosocomial infection, already a serious problem in most hospitals. Infectious pathogenic microorganisms (for example, those of the Pseudomonas and Staphylococcus species) can enter and proliferate within the system and, most often, in the reservoir. Exposure of surgical, traumatic, or pathologic wounds to these pathogens by fluid that leaks from fluid couplings, failed seams in the reservoir or applicator pad, or from the vented reservoir itself, may contribute to the development of secondary infection in the individuals exposed.

The applicator pads used in connection with such devices, for example those described in U.S. Pat. Nos. 3,867,939, 4,114,620, and 4,149,541, also have a number of disadvantages. The most commonly used applicator pads are constructed of flexible polymeric sheeting, formed into conduits for fluid passage. More specifically, U.S. Pat. No. 3,867,939, describes a widely used disposable applicator pad for medical application. The pad is of a laminate construction, with outer layers of absorbent material bonded to a polymeric inner layer that forms a conduit for the passage of fluid. Because of the design of this pad, a moist or dry technique can be used when therapy is delivered. However, if the pad is soiled with urine, blood, or other substances, it must be replaced with a clean, new pad since the integral absorbent coverings are not designed to be cleaned or removed. U.S. Pat. Nos. 4,114,620 and 4,149,541 also relate to polymeric laminated applicator pads that contain internal conduits for fluid passage. Although these applicator pads are more easily cleaned than those described above, they are uncomfortable for the patient, may contribute to skin irritation and cannot be used for moist heat transfer.

From the discussion above, it is apparent that substantial improvement is needed in localized heat or cold transfer devices and applicator pads designed for use in conjunction with such devices. Moreover, the problems described above are not exhaustive. Instead, they are merely examples of difficulties encountered with present devices. Clearly, a new and superior heat transfer device is greatly needed.

SUMMARY OF THE INVENTION

The above-noted and other drawbacks of the prior art are addressed by providing a novel system for effecting selective heat transfer to or from a body part. The new system features a reusable or disposable operably connectionless closed loop applicator module designed for efficient and convenient non-fluid communicating interface with heating and pumping elements. The modular nature of the system advantageously enables contained fluid to be sterilized and remain sterile, or sealed from the atmosphere, and allows the fluid system to be isolated from the housing. The system also reduces or eliminates the need for the undesirable assembly of often leaky connections between a fluid reservoir, applicator pads and conduits therebetween. The present invention provides an integral fluid system requiring no connection of fluid transporting conduits prior to use and in which the fluid system can be completely isolated from the housing and pump. The fluid system, accordingly, is hermetically sealable and may remain filled with fluid whether in use or not in use. The system may be portable, if desired, to facilitate convenient transfer from one location to another by the user or health care professional.

The present invention otherwise comprises a closed loop system employing fluid circulation to effect moist or dry heat transfer to or from various regions of the human or animal body. The system includes a fluid filled flexible applicator pad in connectionless linkage with a fluid circulation system and a mechanism for effecting heat transfer and exchange. Preferably, the pad is constructed of at least two sheets of flexible polymeric sheeting, constructed in such a manner that a number of passages for fluid flow are formed within the interior of the pad. These passages are integrally connected to a closed conduit of finite length. The continuous conduit is operatively interfaced with a fluidless housing having mechanisms to (1) circulate the fluid through the conduit and the pad; (2) to remove heat from or add heat to the fluid; and (3) to control these processes. In a particularly preferred embodiment, the device includes circuitry to allow the selective control and monitoring of temperature in the system, as well as a mechanism for controlling the rate of flow through the conduit.

The invention also provides an improved applicator pad suitable for delivery of moist or dry heat or cold. The pad has a removable, disposable or reusable outer covering affixed to one or more sides of the pad by suitable mechanical means such as snaps, zippers, or the like. This feature allows one to dispose of, replace, or clean the covering, if desired, while reusing the applicator pad.

More specifically, according to the present invention there is provided a system for effecting heat transfer to or from a selected region of the body, comprising an (a) applicator module including a pad having a plurality of flow passages therein, and a closed loop conduit that is integrally joined in fluid communicating relation to the pad so as to permit circulation of a fluid through the flow passages of the pad and the conduit; (b) a housing, having a pump and a heat exchanger operably mounted in the housing; and (c) a mechanism for reversibly engaging the conduit with the housing so as to allow the heat exchanger to selectively heat or cool fluid within the conduit and to allow the pump to circulate fluid through the conduit and flow passages of the pad. In an additional novel and more preferred embodiment, the applicator module includes a cassette that is joined, preferably integrally, in fluid communicating relation to the conduit. The cassette includes a mechanism, device or area for interfacing with the heat exchanger to allow selective transfer of heat or cold from the heat exchanger to a fluid in the cassette. Similarly, the cassette includes a mechanism for operably interfacing with the pump in such manner as to allow the pump to pump fluid through the cassette. Preferably, the cassette also includes a mechanism that allows convenient reversible engagement with the housing.

In one preferred embodiment, the pump comprises a peristaltic pump and the mechanism for interfacing with the pump comprises a flexible tube. Preferably, the heat exchanger comprises a thermoelectric heat pump. A related embodiment includes a pump that circulates fluid through the conduit by peristaltic action and a heat exchanger that comprises a thermoelectric heat pump for producing heat when an electrical potential of one polarity is applied and for absorbing heat when an electrical potential of the opposite potential is applied. In this embodiment, the housing includes a control circuit, which has a temperature sensor for detecting and responding to the temperature of the fluid and which controls the polarity and duration of application of an electrical potential to the thermoelectric heat pump.

In an additional refinement of the invention, the housing includes a fan apparatus and associated power supply. The fan apparatus may be used to remove excess heat from those portions of the system located in the housing section.

In yet an additional embodiment, the cassette defines a plurality of fluid transporting channels that are connected to a bladder in a manner that will allow flow of fluid from the channels to the bladder. The bladder may be a single bladder, or in a preferred embodiment, a series of bladders. An inlet valve and an outlet valve are interposed between the bladder or bladders and the channels. The inlet valve allows fluid to flow into the bladder when fluid pressure inside the bladder is less than the fluid pressure in the channel adjoining the inlet valve, and the outlet valve allows fluid to flow from the bladder when fluid pressure inside the bladder is greater than the fluid pressure in the channels. With this embodiment, the pump functions by alternately increasing and decreasing fluid pressure in the bladder. In a more preferred version of this apparatus, the pump intermittently increases fluid pressure in the bladder by intermittently compressing the bladder, which comprises resilient means, for example, a sponge or spring, for expanding the bladder after compression by the pump.

In a further refinement, the cassette also comprises a plate mounted in such manner that the plate compresses the bladder when force is exerted against the plate. A suitable pump for use in this system comprises a cam rotatably mounted on an axis in a position such that upon rotation about the axis the cam intermittently displaces the plate so as to intermittently compress the bladder. With this pump, fluid does not flow through the pump, but rather through a bladder which is compressed by the pump. The cam may be rotated by any suitable drive mechanism, preferably an electric motor. With this embodiment, the heat exchanger will preferably include a thermoelectric heat pump. The system may also include a temperature control circuit that is capable of responding to the temperature of fluid within the conduit, by controlling the polarity and duration of application of an electrical potential to the thermoelectric heat pump.

In yet a further embodiment, the cassette, which may itself be flexible, comprises a flexible bladder and the pump comprises a compression element mounted in the housing in operative relation to the bladder so that the pump is capable of intermittently compressing the bladder.

In a further alternative embodiment, the pump of the present invention comprises a rotary driver which in turn comprises a motor which rotates a drive magnet. The pump powers an impeller assembly mounted within the cassette to circulate fluid through the closed loop system of the invention. In a preferred embodiment of this type, the applicator module includes the following: a pad defining a flow passage therein; a conduit joined in fluid communicating relationship to the pad so as to enable circulation of a fluid through the flow passage, said conduit having a first segment for receiving the fluid from the flow passage of the pad and a second segment for delivering the fluid into the flow passage of the pad; and a cassette, which is insertable into the housing. The cassette has a first port joined in fluid communicating relationship to the first segment of the conduit and a second port joined in fluid communicating relationship to the second segment of the conduit. The cassette also includes a heat exchange element having a heat conductive casing defining a fluid influx channel, which is in fluid communicating relationship with the first port, and a fluid efflux channel. Disposed within the casing are one or more heat conductive baffles. The cassette further includes an impeller having a responsive member which is responsive to the magnetic field generated by the drive magnet and which rotates with the drive magnet, a impeller cavity in fluid communicating relationship with the fluid efflux channel of the heat exchange element and with the second port, and a hub, linked to the response member so as to rotate with the response member, the hub bearing at least one radially projecting fin which is disposed in the impeller cavity and is sized and shaped so as to pump the fluid through the impeller cavity and through the flow passages of the pad, the conduit, and the passages of the heat exchange element upon rotation of the hub.

Applicator modules made according to the present invention may be either reusable or disposable, and optionally, may be capable of sterilization prior to use.

The invention also includes an improved pad for use in the applicator module. With this embodiment, are included, the pad which may include a plurality of flow passages therein, a covering for the pad, and means for reversibly affixing the covering to one or both sides of the pad in a manner such that the covering may be removed from the pad and replaced with the same or another covering. Preferably, a series of snaps is used for attachment.

Methods for topical heat or cold treatment are also provided. Thus, for example, the invention includes a method of topically treating an animal or human body, which comprises applying a thermiatric bladder to a part of an animal or human body, circulating a liquid through a hermetic flow path which includes the interior of the bladder, and generating a temperature differential in the liquid across the bladder. Also included is a method comprising applying a thermiatric bladder to a part of an animal or human body; peristaltically circulating a liquid through a hermetic flow path which includes the bladder; and changing the temperature of the liquid at a point in the flow path removed from the bladder.

BRIEF DESCRIPTION OF THE DRAWINGS

FIG. 3 is a perspective, partially cutaway, view of an embodiment comprising a housing and cassette constructed in accordance with the invention.

FIG. 4 is an enlarged view of a peristaltic pump.

FIG. 5 shows the device of FIG. 3, partially in phantom, as assembled for operation.

DETAILED DESCRIPTION OF THE PREFERRED EMBODIMENTS

Figure 1:
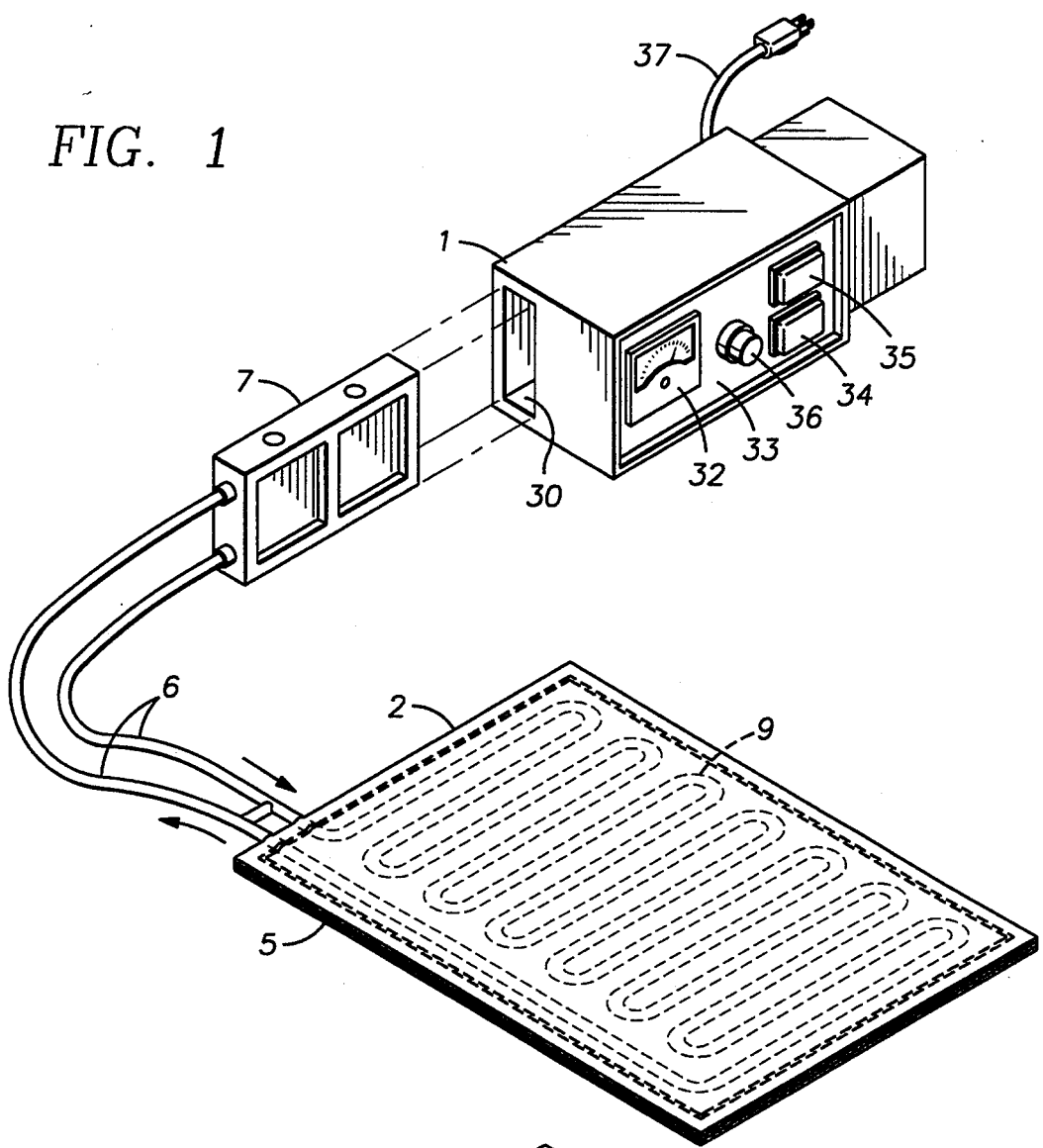
FIG. 1 is a perspective view of a housing and applicator module.

FIG. 1 depicts a general overall view of the present invention. In the device shown, there are a housing 1 and an applicator module 2 for applying heat or cold to a selected body part of an animal or human. The housing comprises a pump and a heat exchanger, which are described in more detail below. The applicator module 2 comprises a closed loop fluid circulation system including an applicator pad 5, a conduit 6, and preferably, a cassette 7 interposed in the conduit. In a preferred embodiment, the cassette 7 is designed to reversibly or retractably engage with the housing and to functionally interface with the pump and heat exchanger. Each of these parts is discussed in more detail below.

Figure 2:
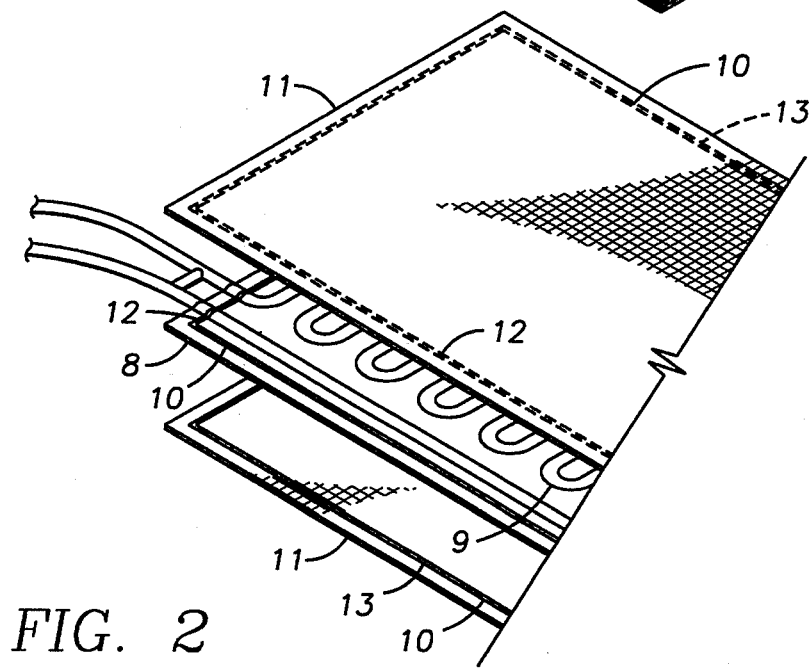
FIG. 2 is an exploded enlarged view of a fragment of an applicator pad.

As shown in FIG. 2, the pad preferably comprises at least two flexible sheets 7 sealed together along their peripheral edges to form a bag or bladder. The sheets are preferably further sealed together so as to form a series of interconnected fluid passageways 9 therebetween. The pad may be made of any suitable flexible material that is resistant to tear or puncture and yet allows efficient heat transfer. Such materials may include but are not limited to plastic or polymeric materials like polyethylene or vinyl polymers. The pad may be disposable or reusable, and it may be flat or contoured to fit a part of the body.

In a preferred embodiment, the pad element of the applicator module may include a mechanism 10 for reversibly attaching a lightweight pad cover 11 or covers to the external surface of one or both sides of the pad. The attachment device depicted in FIG. 2 comprises a groove or series of grooves 12 extending along the periphery and/or other locations on the pad that are designed to reversibly engage a corresponding tongue or series of tongues 13 projecting from the surface of the pad cover or vice versa. Other attachment devices such as snaps, zippers, buttons and the like could also be used. With an attachment device similar to that shown in the drawing, however, the pad cover 11 can be attached to the pad by aligning the tongues 13 in corresponding grooves 12 and then applying pressure to engage the tongue in groove mechanism. Similarly, with a "snap on" attachment mechanism, the covering and pad will each include a plurality of corresponding snaps and the cover may simply be "shaped" onto the pad. Alternatively, adhesive strips, e.g., made of "Velcro" or a similar material may be used.

Preferably, the pad cover 11 will be made of a material that is soft to the touch, non-irritating to the skin, lightweight, and affords efficient heat transfer but also is resistant to wear, tearing, and puncture. Suitable pad coverings include, for example, absorbent material or man-made fabrics such as cottons and non-woven materials. The pad cover 11 may also be designed to allow for dry or moist heat or cold transfer; if moist heat transfer is desired, an absorbent material such as polymeric woven and non-woven material or cottons may be most suitable. Preferably, the material used for manufacture of pad cover 11 will be sufficiently inexpensive so that the pad cover can be disposed of as soiled or after a single use, if desired. In an alternate embodiment, however, the pad cover may be made of a material that can be cleaned and reused. Such a material might be a cotton cloth to which a polymeric material with a tongue or groove is attached around the periphery or at another strategic location.

The novel reversible engagement between pad cover 11 and pad 5 provides the advantage of allowing the pad and pad cover to be dispensed and transported as a unit. It also allows the pad cover to be changed or cleaned, when it becomes soiled without requiring disposal or removal of the pad or any portion of the applicator module. Alternatively, a pad having a covering irreversibly glued, fused, or affixed to its surface (see, e.g., U.S. Pat. No. 3,867,939) may be used with the device shown. Unfortunately, such pads do not afford a number of the advantages of the novel pad and pad cover set described herein and thus are less preferred for use.

Returning now to FIG. 1, it should be noted that the applicator pad 5 is integrally or hermetically connected to the closed loop conduit 6 in such manner as to allow free flow of fluid from passageways 9 in the pad through the conduit 6 and vice versa. By integrally connecting the pad and the closed loop conduit, one reduces or avoids the need for threaded joints or other mechanical connectors typically needed to fill and make up a pad. The hermetic nature of the integrated structure greatly reduces the inconvenience of assembly and the potential for leaks and contamination of fluid in the pad. Consequently, patients are much less likely to develop nosocomial infections when using the pads of the invention.

The conduit 6 may be made of a number of plastic or rubber materials that preferably are resistant to kinking and deformation that causes decreased flow through the conduit. The conduit is preferably flexible and compressible. The conduit may be designed so as to directly interface with the pump and heat exchanger in a manner that allows efficient transfer of heat to or from fluid in the conduit and circulation of such fluid through the conduit and passages of the pad. Portions of the conduit sections may further be insulated with foam, cloth, or other material to help prevent unwanted heat transfer from occurring at points between the pad and pump. Use of such insulation has been found particularly effective when applied around the tubing section leading from the pump to the pad.

In an embodiment that is highly preferred, the applicator module also comprises a cassette 7, which is joined in fluid communicating relation to the conduit. Thus, in the embodiment shown, the applicator pad 5, conduit 6, and cassette 7 are integrally linked to comprise a closed loop system for fluid circulation, which may be filled with fluid and sterilized as a unit if desired.

Figure 16:
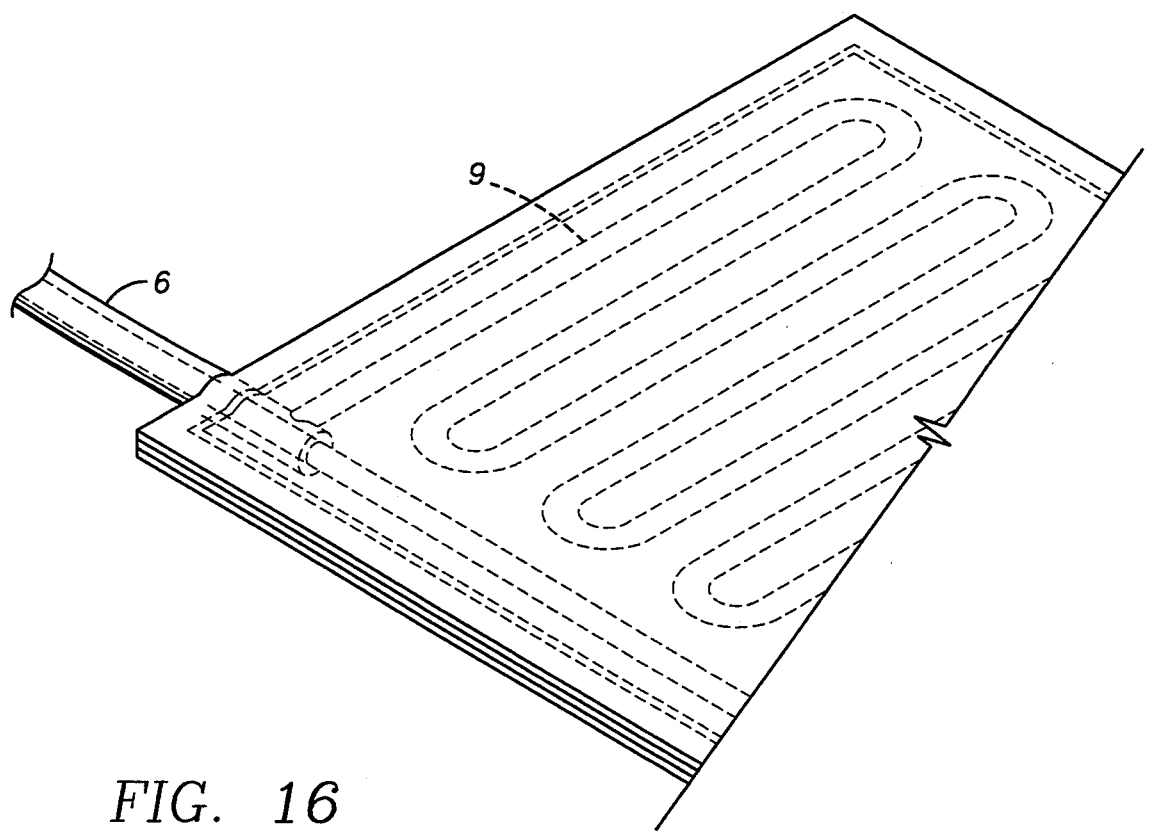
FIG. 16 is a side view of a pad with coaxial conduit segments.

In an alternative embodiment, shown in exemplary form by FIG. 16, conduit 6 may comprise coaxial tubing in which one conduit segment is placed to be substantially concentric within the other conduit segment. The end of a coaxial conduit segment may transition to permit separate conduit flow lines, as FIG. 16 illustrates, by passing the internal segment through the wall of the exterior segment while ensuring said exterior segment wall remains leakproof.

In the device shown in FIG. 1, various cassettes 7 are designed to interface the housing, e.g., by insertion into a slot or opening in the body of the housing, in such a manner as to allow operative interface between the cassette heat exchanger and pump mounted in the housing 1. The cassette may have a variety of forms, three of which are described in more detail below.

FIG. 3 illustrates a cassette that comprises a flexible region of conduit 14 designed so as to interface with a peristaltic pump 15, which is shown in more detail in FIG. 4. The peristaltic pump comprises a plurality of freely rotatable orbital rollers 16 mounted between end plates 17 driven in rotation by a shaft 18. The flexible section of conduit 14 is arranged in a race through the pump which is spaced from the outer ends of the rollers 16 a distance sufficient to permit collapse of the conduit 14 as the shaft 18 turns. The orbital rollers 16 are moved to first compress the flexible conduit 14, thereby forcing a quantum of fluid trapped in it along the direction of movement of the orbital rollers 16 and causing movement of fluid through the closed loop system.

As shown in FIGS. 3 and 5, the cassette also includes a bladder 20, which may simply comprise an additional section of a flexible or rigid material such as plastic tubing or maybe made of a variety of different materials specifically designed to enhance heat transfer, such as copper or aluminum, or a polymer with efficient heat transfer characteristics. The bladder is designed to contact or engage a heat exchanger 21 mounted in the housing in such manner as to allow effective transfer of heat or cold from the heat exchanger to the bladder.

Preferably, the heat exchanger 21 is bifunctional and can be used for selective delivery of either heat or cold. However, devices capable of delivering only heat or only cold are also included within the scope of the invention. A number of suitable heat exchangers may be used, including, for example, electric resistor heat exchanger, mechanical heat pump, absorption refrigerators, or thermoelectric resistor strips. However, a thermoelectric heat pump or a bank of thermoelectric heat pumps connected in branches or in series capable of selectively delivering heat to or removing heat from the system is preferred. Solid state thermoelectric heat pumps have numerous advantages over separate heating and cooling systems. Generally, thermoelectric heat pumps operate by absorbing heat on one side and radiating the same amount of heat, plus any heat due to resistive heating, on the other side. When polarity is reversed, the opposite sides absorb and radiate heat. A thermoelectric heat pump may be configured as a flat plate or plates disposed in heat communicating relation to one or both surfaces of the heat exchange interface element 20. Particularly preferred is a heat pump such as the Duratec TM DT 1069 Thermoelectric Cooler sold by Marlow Industries, Inc., 10451 Vista Park Road, Dallas, Tex. 75238-1645.

Figure 6:
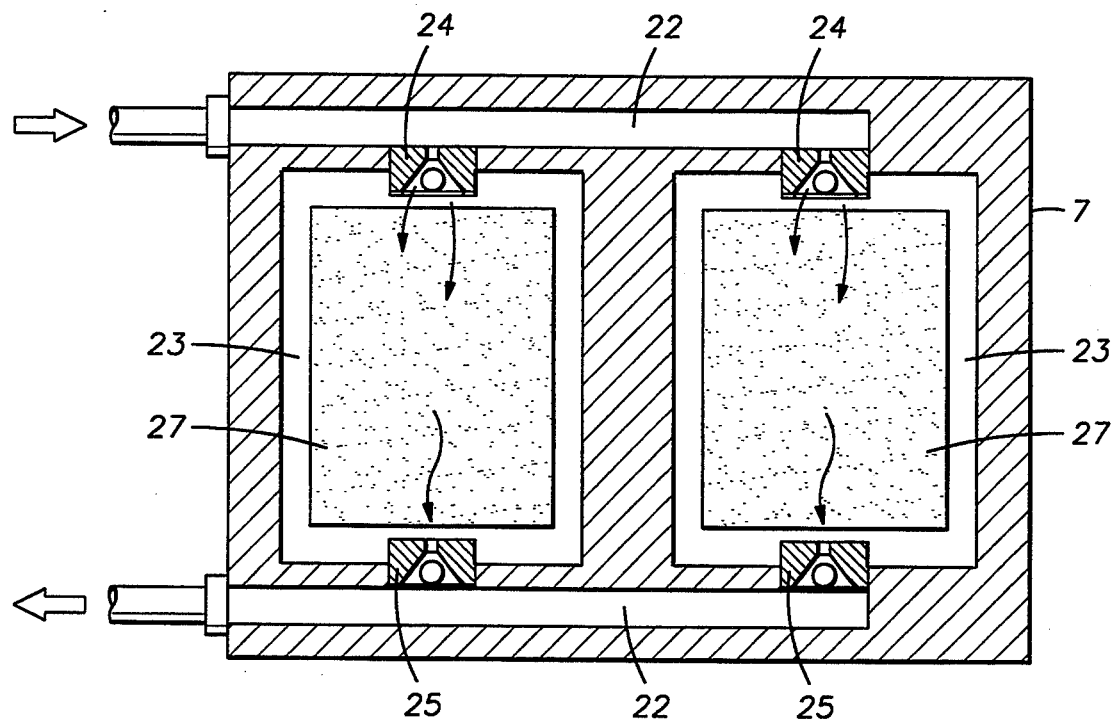
FIG. 6 is a partially cutaway, sectional view of a cassette, taken along section line 6—6 in FIG. 7.
Figure 7:
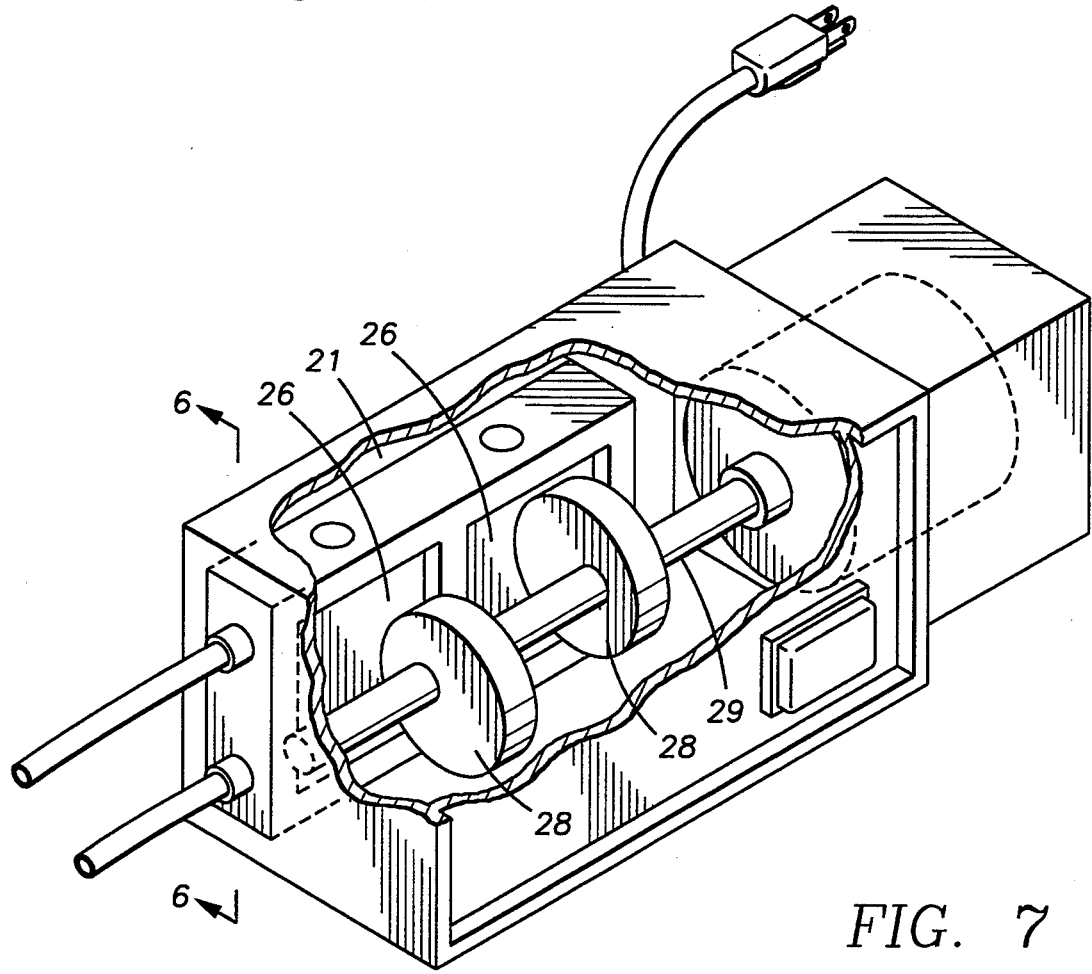
FIG. 7 is a perspective, partially cutaway, view of an embodiment comprising a housing and cassette constructed in accordance with the invention.
Figure 8:
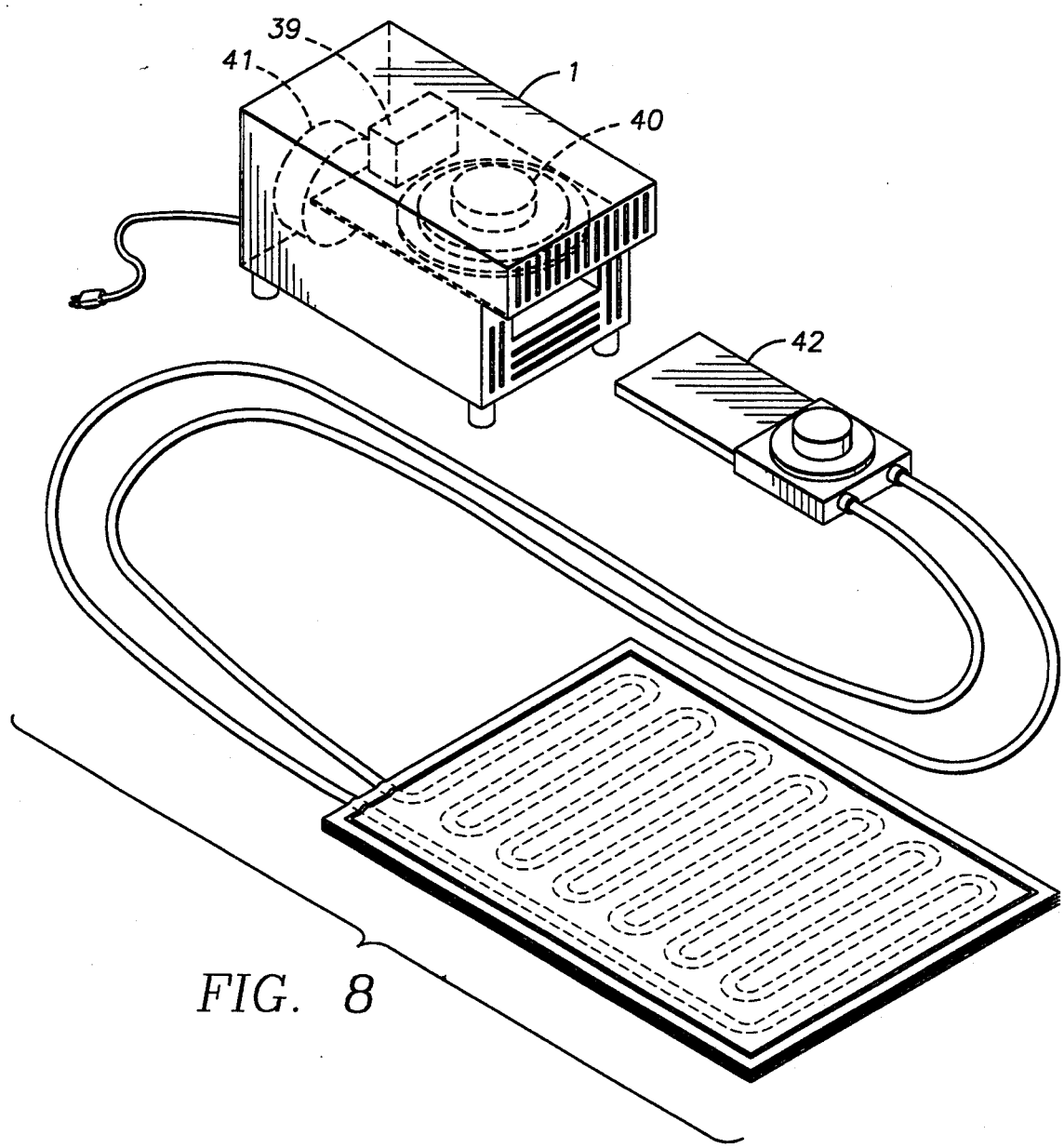
FIG. 8 is a perspective view of a housing and applicator module in an embodiment employing a rotary driver with drive magnet.

In an alternative embodiment, shown in FIGS. 6 and 7, the cassette 7 defines a fluid transporting channel or channels 22 interconnected to a bladder or bladders 23 by an inlet valve 24 and an outlet valve 25. The design of inlet valve 24 allows fluid to flow into the bladder 23 when the fluid pressure inside the bladder is less than the fluid pressure in the channel; similarly, outlet valve 25 allows fluid to flow from the bladder when the fluid pressure inside the bladder 23 is greater than fluid pressure in the channels 22. Valves of the type commonly known as check valves are preferred, however other suitable valves would include those known as "one-way valves" of flutter valves.

The cassette shown in FIG. 7 comprises a series of two tandem bladders, each of which has at least one plate 26 formed of a relatively rigid material such as aluminum or hard plastic. The plate 26 is mounted in such a manner as to allow it to be displaced into the body or cavity of the bladder when force is exerted against it from the exterior of the bladder and, conversely, to allow it to return to its precompression position when the force is removed. Preferably, the bladder 23 also comprises a resilient member 27 for facilitating or effecting the latter function. In a preferred embodiment, this resilient member will comprise a sponge disposed inside the cavity defined by the bladder; however, springs or other resilient means could also be used.

The pump functions by intermittently displacing the plate 26, thereby compressing the bladder, and causing fluid flow through the channels defined by the cassette, the conduit and the flow passages of the pad. The pump may, for example, comprise a motor driven cam 28 rotatably mounted on an axis 29 in a manner such that rotation of the cam about its axis alternatively exerts and releases a force against plate 26 so as to cause intermittent compression of the bladder. When the bladder is compressed, the fluid pressure in the bladder is greater than the fluid pressure in the channels so that outlet valve 25 is forced open while inlet valve 24 at the other end is closed and fluid flows from the chamber or bladder into the channels located in the cassette. Preferably, when tandem bladders are present, the bladders will be compressed in alternating fashion so as to provide a more even flow of fluid through the closed loop system. Additional bladders may be added if desired.

In the embodiment shown, the heat exchanger 21 may be designed so as to interface with the cassette at one or both sides of bladder 23, but preferably with the side of the bladder opposite plate 26. In a preferred embodiment, the heat exchanger 21 comprises a flat surface lying adjacent the side of the bladder opposite plate 26. Accordingly, it is preferred that the surface of the bladder adjacent the heat exchanger by made of a material conducive to efficient heat transfer such as copper or aluminum.

In yet a further embodiment, the cassette may be made of a flexible polymeric material and thereby comprise a flexible cassette, having a bladder or a series of bladders in tandem. Like the embodiments shown in FIGS. 6 and 7, the flexible cassette defines a fluid transporting channel or channels 22 interconnected to a bladder or bladders 23 by an inlet valve 24 and an outlet valve 25, as previously described. With the flexible cassette, valves of the type known as "flutter valves" are preferred.

The flexible cassette differs from its counterpart shown in FIGS. 6 and 7 in that it will generally not include plate 26. Instead, the plate, or another suitable compression element such as a roller bar or cam, is provided in operative relation to the bladder so as to be capable of intermittently compressing the bladder. In a preferred embodiment, the compression element includes a plate mounted on an axis in the housing in such a manner as to allow it to intermittently compress the bladder. In an even more preferred embodiment, a thermoelectric heat pump is affixed to the surface of the plate.

A further alternative embodiment of the present invention is displayed in FIGS. 8 through 15. In this embodiment, the pump comprises a rotary driver which rotates a drive magnet. A particularly preferred drive magnet for this application would be a magnetic cup. The pump powers an impeller mounted within the cassette to circulate fluid through the closed loop system of the invention. In a particular refinement, shown in FIG. 8, housing unit 1 comprises a cooling fan power supply 39, a motor 40, cooling fan unit 41, and an opening to engage cassette unit 42. An example of a suitable power supply is the VS75-15 model, V-series power supply marketed by Lambda Electronics, Inc. of 515 Broad Hollow Rd., Melville, N.Y. 11747 (516) 694-4200. An example of a suitable fan is the Model 4850X miniature axial fan marketed by Papst Mechatronic Corp., Aquidneck Industrial Park-T, Newport, R.I. 02840 (401) 849-8810.

Figure 9A:
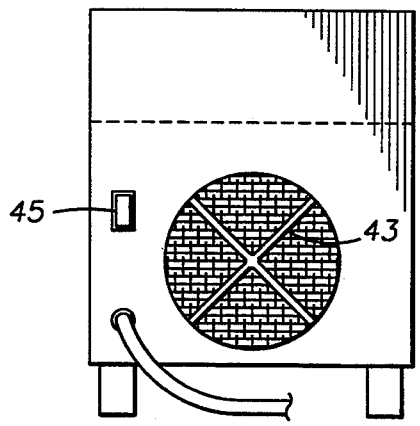
FIGS. 9A and 9B are end views of the housing section of the invention in an embodiment employing a rotary driver with drive magnet.
Figure 9B:
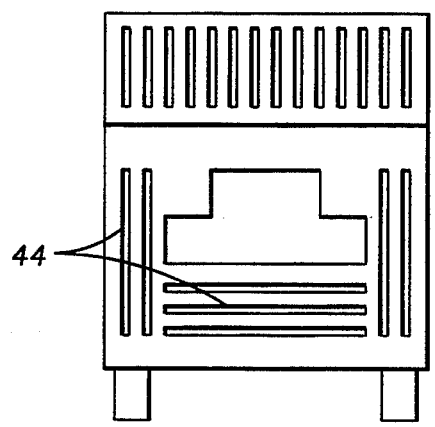

As can be seen in FIGS. 9A and 9B, cooling fan unit 41 may be provided with a screen or grill 43 which, together with vents 44, will permit air to enter and leave the housing unit. The invention may be turned on and off, or be otherwise controlled, by use of switch 45. FIG. 9B is an exemplary view of the housing unit while it is not engaged with the cassette.

Figure 10:
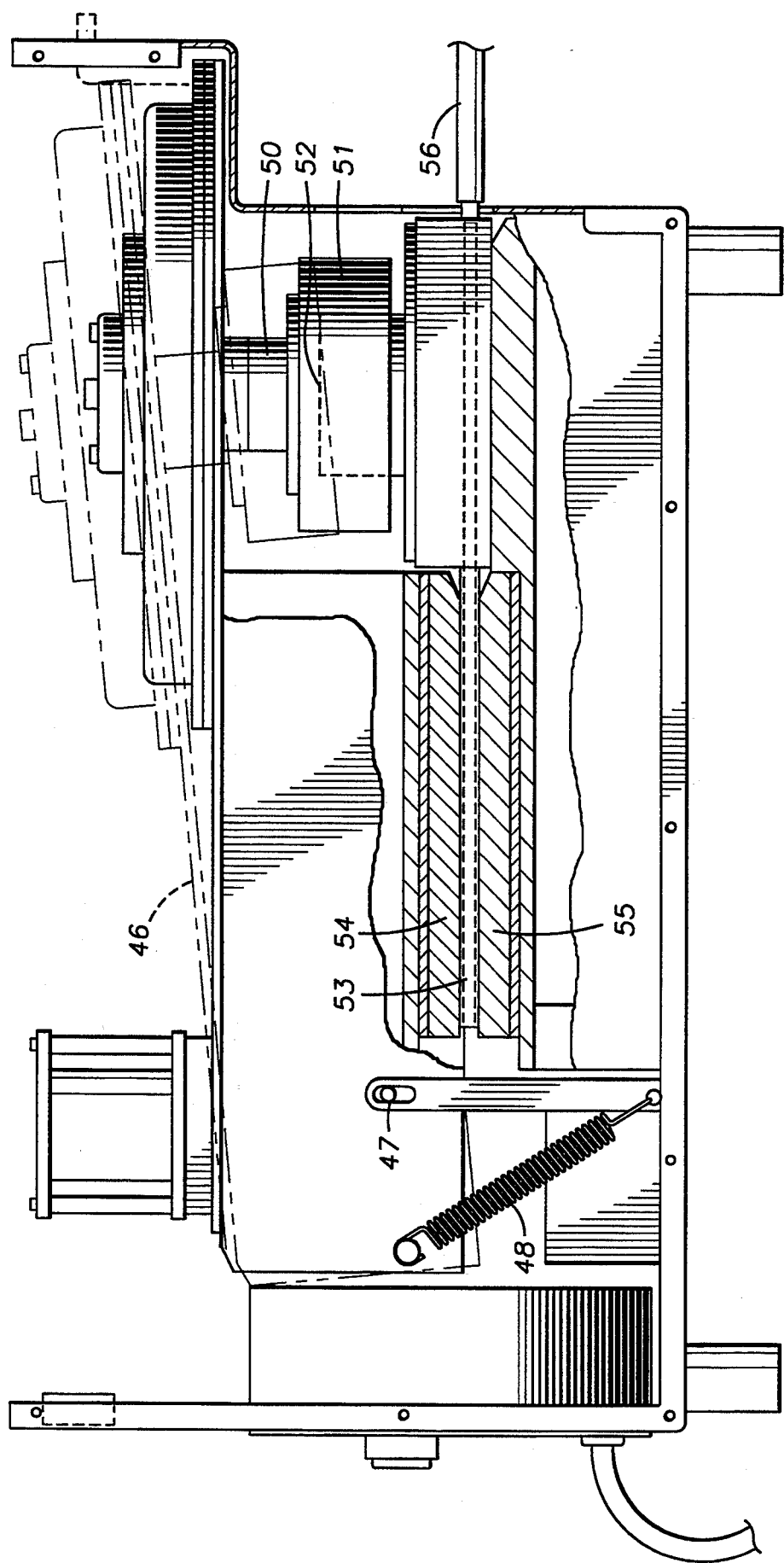
FIG. 10 is partial cutaway view which illustrates insertion of the cassette into the housing section of an embodiment of the invention which employs a rotary driver with a drive magnet.

FIG. 10 illustrates an operational interconnection between the housing unit and the cassette. In this configuration, the housing unit may be provided with a hingeably attached cover 46. Cover 46 is attached at pivot points 47 to the housing unit. Additionally, a tension device, such as spring 48 may be attached to the housing unit and cover to assist in lifting the cover. Cover 46 includes rotary driver comprising motor 40 which may be seen in greater detail in FIGS. 11 and 12.

Motor 40 includes a drive shaft housing 50 which adjoins drive magnet 51. An example of a suitable motor for this application is the 12FP Ferrite Series DC Servo Motor marketed by PMI Motion Technologies, 49 MaLL Drive, Commack, N.Y. 11725 (516) 864-2084. Drive magnet 51 is designed to at least partially enshroud cassette cap 52 when the cassette is placed within the housing. In this position, the cassette heat exchange element 53 is disposed between upper and lower heat exchangers 54 and 55. Conduit sections 56 extend through an opening in the housing unit.

Figure 11:
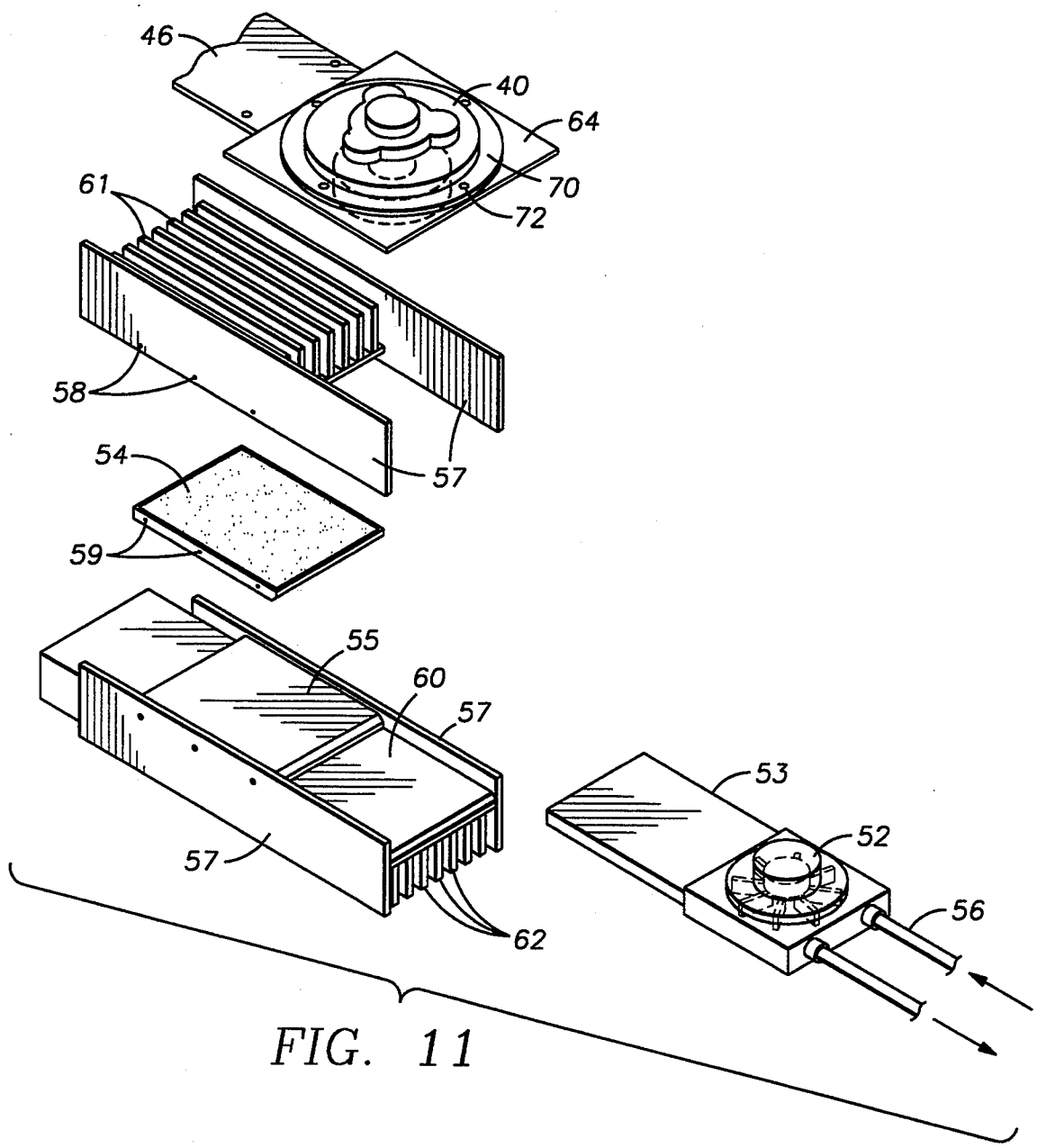
FIG. 11 is an exploded view of the housing and cassette sections of an embodiment of the invention which employs a rotary driver with a drive magnet.

The heat transfer aspects of this embodiment may be understood and appreciated from the exploded view provided by FIG. 11, which shows a preferred embodiment having a pair of heat exchangers with the heat exchange element interposed therebetween. Upper heat exchanger 54 may be fixedly disposed between side walls 57 of the housing unit. Those skilled in the art will recognize numerous means for fixedly disposing exchanger 54. As depicted here, however, the exchanger may be affixed to side walls 57 by means of screws, bolts, rivets or similar fasteners which will pass through holes 58 in the side walls and into openings 59 in the exchanger.

Lower heat exchanger 55 and plate 60 are fixedly disposed to side walls 57 in a like manner. FIG. 11 shows exchanger 55 in a fixed relation to side walls 57. Adjoining the upper and lower heat exchangers, and disposed between side walls 57, are upper and lower serrated cooling fins 61 and 62. The fins may be made of any of a number of heat conductive materials, such as copper, aluminum, etc.

Figure 12:
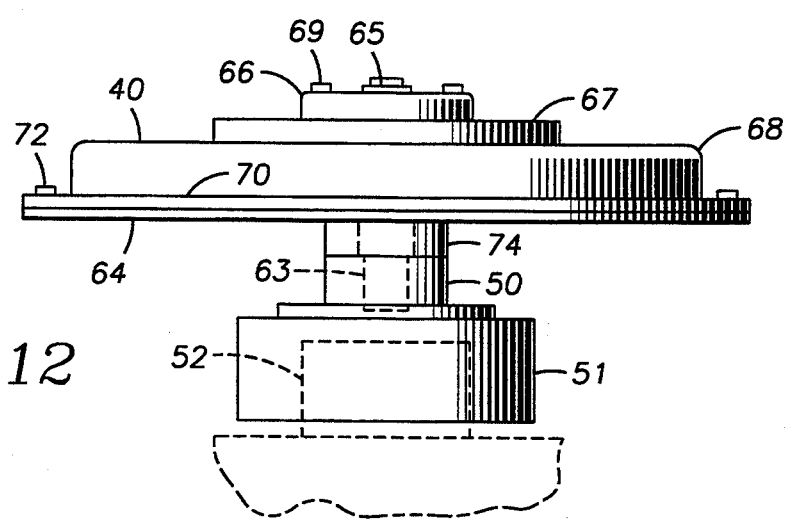
FIG. 12 is side view of the rotary driver and drive magnet.

The rotary driver, as shown in FIGS. 11 and 12, may be integral with cover 46 of the housing unit. A rotary driver is mounted so that drive shaft 63 of motor 40 passes completely through mounting plate 64. At its top, the drive shaft comprises a head 65 which is supported by support plate 66. Support plate 66 adjoins upper motor cover plate 67 which, in turn, adjoins lower cover plate 68. Support plate 66 may be held in place with the use of screws, bolts or similar fasteners 69. Lower motor cover plate 68 may be held in place with a mounting ring 70 which is fastened to mounting plate 64 using bolts, screws or similar fasteners 72. Mounting plate 64 is, in turn, fixedly attached to cover 46.

The bottom end of drive shaft 63 extends below mounting plate 64. This portion of drive shaft 63 is encased by drive shaft housing 50 and collar 74. Washer/spacers (not shown) may be axially placed along the drive shaft between drive shaft housing 50 and collar 74 and between collar 74 and mounting plate 64. A washer/spacer (not shown) may also be placed axially along drive shaft 63 between upper and lower motor cover plates 67 and 68. Placement of these washer/spacers will help provide for proper alignment of the drive shaft during rotation.

The cassette used in this embodiment is shown in a partial phantom perspective view in FIG. 11. Its features are shown with greater particularity in FIGS. 13, 14 and 15. The cassette includes a heat exchange element and an impeller.

In the embodiment shown, the impeller includes first and second ports 75 and 76, a number of tubular openings, and an impeller cavity 88. Port 75 communicates with a fluid influx channel 77 of the heat exchanger via tubular openings 78 and 79 in the impeller body. A fluid efflux channel of the device 80 is communicates with tubular openings 81. As may be seen in FIGS. 13 and 14, tubular opening 81 communicates fluid into a lower chamber 91 of impeller cavity. 88. Impeller cavity 88 is divided into lower chamber 91 and upper chamber 93 by a fluid permeable member such as disk 92 which is centrally apertured to permit transfer of fluid between the upper and lower chambers. Fluid may be communicated from upper chamber 95 through tubular opening 82 at the periphery of said upper chamber.

The device may also include heat exchange element access means consisting of valves, openings, gates, or similar structures which will regulate passage of fluid from the impeller to the heat exchange element section and vice versa.

The impeller further comprises a central axis 83 and a hub 84 which may freely rotate around axis 83. Hub 84, in turn, carries one or more radially projecting fins 85. The impeller also comprises a response member such as an axial response magnet 86 situated so as to magnetically respond to a field generated by drive magnet 51.

The impeller further comprises a covering 87 to enclose the above described structures and contain fluid. The covering forms impeller cavity 88 to contain fluid.

Figure 15:
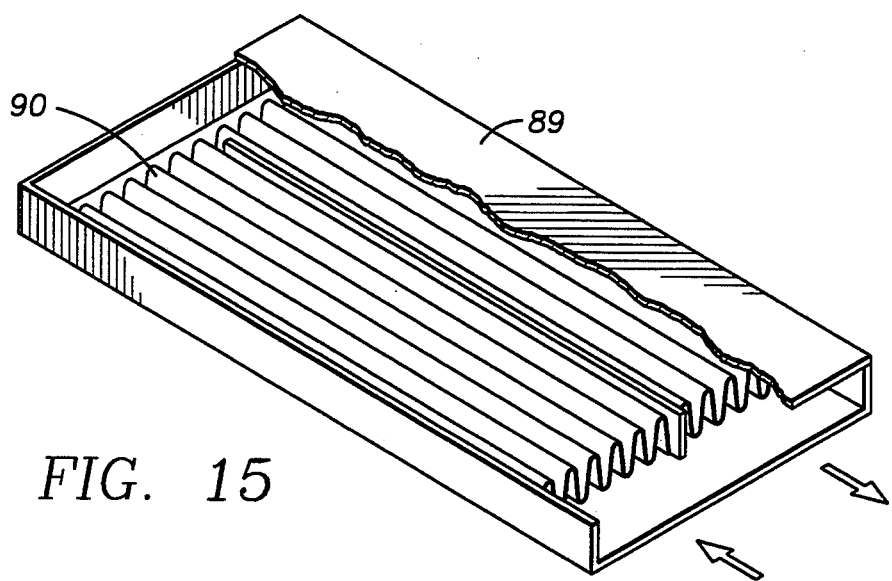
FIG. 15 is sectional, partially cutaway view of the heat exchange element portion of a cassette.

The heat exchange element comprises a casing 89 which encloses one or more fluid channels. FIG. 15 illustrates an exemplary embodiment for defining flow passages within the channels by enclosing a heat conductive corrugated member 90 within the casing to form a series of baffles around which the fluid passes.

Figure 13:
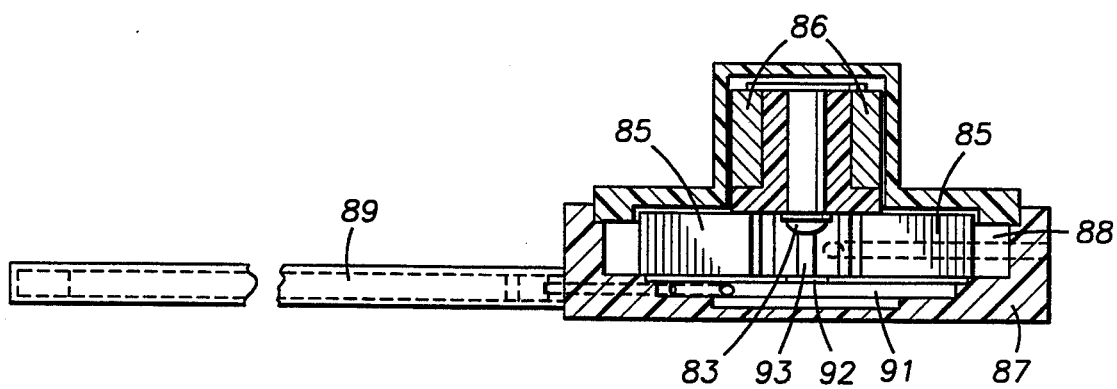
FIG. 13 is a sectional side view of a cassette.
Figure 14:
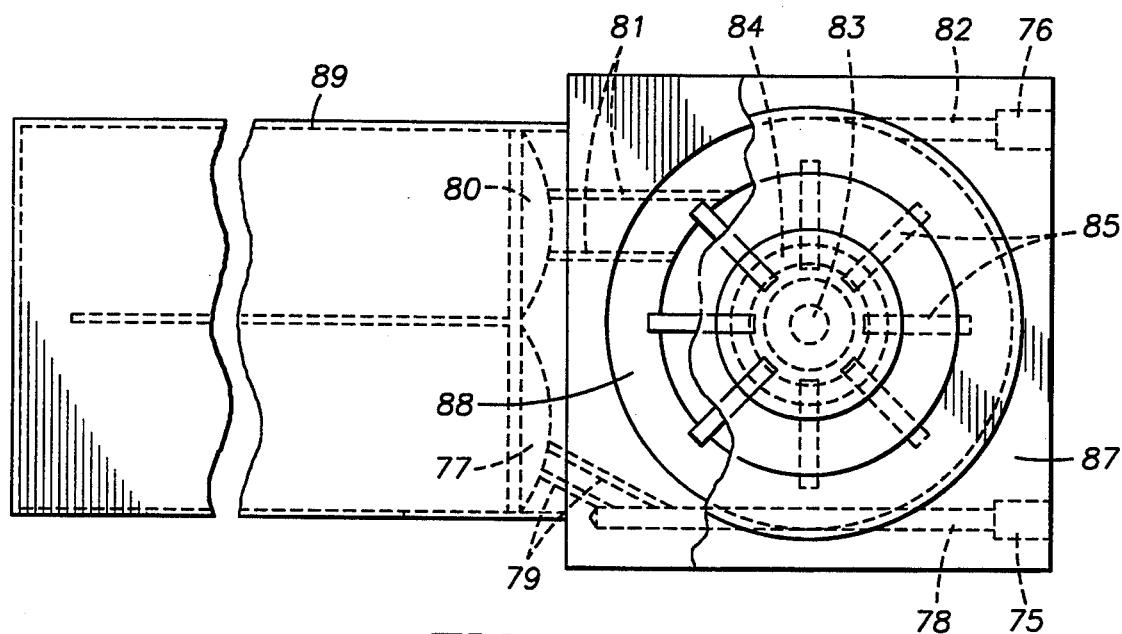
FIG. 14 is a top view, partially in phantom, of a cassette.

In operation, the impeller of the cassette receives fluid through a first port 75, as shown in FIG. 14. The fluid is communicated along tubular openings 78 and 79 into the fluid influx channel 77 and through the heat exchange element. The arrows in FIG. 15 demonstrate the general flow of fluid through the passages formed by casing 89 and corrugated member 90 within the heat exchange element section. While within the heat exchange element, the fluid will gain or lose heat through the walls of casing 89 as a result of contact with upper and lower heat exchangers 54 and 55. As shown in FIGS. 13 and 14, fluid exits the heat exchange element through fluid efflux channel 80 and is communicated through openings 81 into the lower chamber 91 of impeller cavity 88. Fluid will then pass through the central aperture of disk 92 and enter upper chamber 93. Rotation of hub 84 and fins 85 causes entering fluid to flow toward the periphery of upper chamber 93 where a portion of the fluid will exit the chamber through opening 82. Fluid finally reenters conduit section 56 via outlet port 76.

Those skilled in the art will recognize that the motor, drive magnet, and response member may be rotated in the opposite direction so that the hub and projecting fins cause the fluid to flow in the opposite direction from that described here.

The heat exchange element portion of the cassette is preferably constructed of materials which will promote efficient transfer of heat to or from fluid within the heat exchange element. Such materials include metals such as copper or aluminum.

In the embodiment shown by FIGS. 8–15, the fluid is moved through the cassette by operation of the impeller. When the cassette is inserted into the housing unit, cassette cap 52 is enshrouded by drive magnet 51. Rotation of drive magnet 51 by means of motor 40 will impart rotation to hub 84 of the impeller. Radially projecting fins 85 will generate fluid pressure to cause the fluid to flow within impeller cavity 88 as well as through inlet and outlet ports 75 and 76 and through the heat exchange element.

An attractive feature of all types of cassettes is the ease and convenience with which they may reversible engage or disengage the housing unit. In the embodiment shown in FIG. 1, the engagement mechanism of the housing 1 comprises a slot 30 into which the cassette may be inserted. Of course, the configuration of the slot may be varied in keeping with the size and structure of the cassette. For example, with the cassette shown in FIG. 3, one end of the housing is left open and the slot 30 extends a distance into one side of the device.

An alternate method of cassette insertion is illustrated in FIG. 10. Insertion of the cassette assembly into the housing in this embodiment requires hinged cover 46 to be lifted at the end incorporating the rotary driver so that said cover rotates angularly about pivot points 50. Following insertion of the cassette, the cover and rotary driver are replaced to their original position. In a modification of this embodiment, the raised cap portion would be flattened so that the rotary driver need not be displaced during insertion or removal of the cassette and the cassette can be slidingly inserted and removed.

Alternatively, the slot may be omitted, and the cassette directly abutted to an open end of the housing. If desired, the housing and cassette may be supplemented with additional closure devices, for example a clasp, hatch or catch 31.

As shown in FIG. 1, in addition to the pump and heat exchanger, the housing 1 preferably includes a number of other features designed to facilitate safe, efficient, reliable, and convenient operation and service of the device. Such features may include, for example, a temperature sensing mechanism 32 such as a thermistor or thermostat in temperature sensing relation to a control circuit 36 for controlling the temperature in the system, a plate panel 33, having an on-off switch 34, and a hot-cold switch for controlling the heat exchanger and adding or removing heat from the system 35. Suitable examples of those features are well known in the art.

Preferably, both the pump and the heat exchanger are electrically powered. Therefore, the housing may also include an electrical connection 37 for imputing power to the system from a battery, electrical outlet or other power source such as an automobile cigarette lighter.

The foregoing description of the invention has been directed to particular preferred embodiments in accordance with the requirements of the patent statutes and for purposes of explanation and illustration. It will be apparent, however, to those skilled in the art that many modifications and changes may be made without departing from the scope and the spirit of the invention.

For example, numerous heat exchanger, pumps and housing configurations may be used. In addition, the form of cassettes utilized may vary from the devices set forth in the drawings. It is apparent that the invention may also be utilized, with other suitable modifications within the state of the art. It is intended in the following claims to cover all such equivalent modifications and variations which fall within the spirit and scope of the invention.

What is claimed is:

1. A device for effecting heat transfer to or from a selected region of a body, comprising:
    (a) a housing having a rotary driver and a heat exchanger operably mounted therein;
    (b) an applicator module which includes;
        (i) a pad defining a flow passage therein;
        (ii) a conduit joined in fluid communicating relationship to the pad so as to enable circulation of a fluid through the flow passage of the pad and the conduit; and (iii) a cassette joined in fluid communicating relationship to the conduit, the cassette having a heat exchange element, which interfaces with the heat exchanger in such manner as to enable selective transfer of heat to or from the heat exchanger to or from a fluid within the cassette, and an impeller for operably interfacing with the rotary driver in such manner as to pump fluid through the applicator module.

2. The device of claim 1 wherein said applicator module circulates fluid within a connectionless closed loop.

3. The device of claim 1 wherein the rotary driver comprises a motor which rotates a drive magnet and the impeller is operationally responsive to the magnetic field generated by the drive magnet.

4. The device of claim 3 wherein the motor is operably attached to the drive magnet by a drive shaft.

5. The device of claim 3 wherein the impeller comprises a magnetic response member connected to a rotatable hub having at least one radially projecting fin.

6. The device of claim 1 wherein the heat exchange element comprises a heat conductive casing defining a fluid channel and one or more heat conductive baffles disposed within said casing so as to allow fluid passage through the channel.

7. The device of claim 6 wherein said baffle or baffles comprises a corrugated member.

8. The device of claim 1 wherein the housing further comprises a hinged cover within which the rotary driver is mounted, said cover being angularly displaceable from the housing to permit insertion of the cassette into the housing.

9. The device of claim 8 wherein the drive magnet is sized and shaped to at least partially enshroud said response member when said cassette is inserted into said housing and said hinged cover is not angularly displaced.

10. The device of claim 5 wherein the cassette is slidingly insertable into the housing.

11. The device of claim 1 wherein portions of said conduit are insulated.

12. The device of claim 1 wherein said conduit is coaxial.

13. An applicator module adapted for use in a heat transfer device, said device having a housing having a rotary driver and a heat exchanger operably mounted therein, comprising:

(a) a pad, adapted for application to a selected region of a body, defining a flow passage therein;

(b) a conduit joined in fluid communicating relationship to the pad so as to enable circulation of a fluid through the flow passage of the pad and the conduit; and (c) a cassette joined in fluid communicating relationship to the conduit, the cassette having a heat exchange element, which interfaces with the heat exchanger in such manner as to enable selective transfer of heat to or from the heat exchanger to or from a fluid within the cassette, and an impeller for operably interfacing with the rotary driver in such manner as to pump fluid through the applicator module.

14. The device of claim 13 wherein said applicator module circulates fluid within a connectionless closed loop.

15. The device of claim 13 wherein the impeller comprises a magnetically responsive member connected to a rotatable hub having at least one radially projecting fin.

16. The device of claim 13 wherein the heat exchange element comprises a heat conductive casing defining a fluid channel and one or more heat conductive baffles disposed within said casing so as to allow fluid passage through the channel.

17. The device of claim 16 wherein said baffle or baffles comprises a corrugated member.

18. The device of claim 13 wherein portions of said conduit are insulated.

19. The device of claim 13 wherein said conduit is coaxial.

20. A device for effecting heat transfer to or from a selected region of the body, comprising:

(a) a housing, which houses a heat exchanger and a motor which rotates a drive magnet; and (b) a closed loop applicator module, which includes, (i) a pad defining a flow passage therein, (ii) a conduit joined in fluid communicating relationship to the pad so as to enable circulation of a fluid through the flow passage, said conduit having a first segment for receiving the fluid from the flow passage of the pad and a second segment for delivering the fluid into the flow passage of the pad, and (iii) a cassette, which is insertable into the housing and includes, a first port joined in fluid communicating relationship to the first segment of the conduit and a second port joined in fluid communicating relationship to the second segment of the conduit, a heat exchange element having a heat conductive casing defining a fluid influx channel, which is in fluid communicating relationship with the first port, and a fluid efflux channel, and, disposed within the casing, one or more heat conductive baffles, and an impeller having a response member which is responsive to the magnetic field generated by the drive magnet and which rotates with the drive magnet, an impeller cavity in fluid communicating relationship with the fluid efflux channel of the heat exchange element and with the second port, and a hub, linked to the response member so as to rotate with the response member, the hub bearing at least one radially projecting fin which is disposed in the impeller cavity and is sized and shaped so as to pump the fluid through the impeller cavity and through the flow passages of the pad, the conduit, and the passages of the heat exchange element upon rotation of the hub.

21. The device of claim 20 wherein portions of at least one conduit segment are insulated.

22. The device of claim 20 wherein the first and second segments of said conduit are coaxially concentric.

23. The device of claim 20 wherein said impeller cavity is divided into a plurality of chambers by a permeable member.

24. The device of claim 20 wherein said housing further comprises:

(a) a serrated cooling fin positioned adjacent said heat exchanger; and (b) an exhaust fan, positioned so as to circulate air through said serrated cooling fin.

25. A device for effecting heat transfer to or from a selected region of a body, comprising:
(a) a housing, which houses a heat exchanger and a motor which rotates a drive magnet; and
(b) a connectionless closed loop applicator module, which includes,
  (i) a pad defining a flow passage therein,
  (ii) a conduit joined in fluid communicating relationship to the pad so as to enable circulation of a fluid through the flow passage, said conduit having a first segment for receiving the fluid from the flow passage of the pad and a second insulated segment for delivering the fluid into the flow passage of the conduit, and
  (iii) a cassette, which is insertable into the housing and includes,
    a first port joined in fluid communicating relationship to the first segment of the conduit and a second port joined in fluid communicating relationship to the second insulated segment of the conduit,
    a heat exchange element having a heat conductive casing defining a fluid influx channel and a fluid efflux channel which is in fluid communicating relationship with the second port, and, disposed within the casing, one or more heat conductive baffles, and
    an impeller having a response member which is responsive to the magnetic field generated by the drive magnet and which rotates with the drive magnet, an impeller cavity divided into a plurality of chambers by a permeable member and in fluid communicating relationship with the first port and with the fluid influx channel of the heat exchange element, and a hub, linked to the response member so as to rotate with the response member, the hub bearing at least one radially projecting fin which is disposed in the impeller cavity and is sized and shaped so as to pump the fluid through the impeller cavity and through the flow passages of the pad, the conduit, and the passages of the heat exchange element upon rotation of the hub.

26. The device of claim 25 wherein said housing further comprises:
(a) a serrated cooling fin positioned adjacent said heat exchanger; and
(b) an exhaust fan, positioned so as to circulate air through said serrated cooling fin.

27. A heat transfer device for selectively transferring heat to or from regions of a body, said heat transfer device comprising:
a. a housing;
b. a pump operably mounted within the housing;
c. a heat exchanger operably mounted within the housing;
d. a separable applicator module which includes:
  1) a flexible applicator pad defining at least one flow passage therein;
  2) a flexible conduit joined in fluid communicating relationship to the pad to permit circulation of a fluid through the conduit and flow passage of said pad;
  3) a cassette joined in fluid communicating relationship to the conduit, the cassette including a mechanism for interfacing with the heat exchanger so as to enable selective transfer of heat to or from the heat exchanger to or from a fluid within the cassette and a mechanism for operably interfacing with the pump so as to enable the pump to pump fluid through the applicator module; and
e. a mechanism for engaging the cassette with the housing so as to allow the heat exchanger to add or remove heat from a fluid within the cassette and the pump to pump fluid through the cassette and into the flow passage of the pad and conduit.

28. The heat transfer device of claim 27 wherein the cassette comprises a heat exchange element.

29. The heat transfer device of claim 28 wherein the applicator module contains a fluid.

30. The heat transfer device of claim 28 wherein the pad further comprises:
a. a covering for the pad; and
b. means for reversibly affixing the covering to the pad in a manner such that the covering may be removed from the pad.

31. The heat transfer device of claim 28 wherein the pad is reusable.

32. The heat transfer device of claim 28 wherein the pad is disposable.

33. A separable applicator module adapted for use in a heat transfer device having a housing with a pump and heat exchanger operably mounted therein, said applicator module including:
a. a flexible applicator pad defining at least one flow passage therein;
b. a flexible conduit joined in fluid communicating relationship to the pad to permit circulation of a fluid through the conduit and flow passage of said pad;
c. a cassette joined in fluid communicating relationship to the conduit, the cassette including a mechanism for interfacing with the heat exchanger so as to enable selective transfer of heat to or from the heat exchanger to or from a fluid within the cassette and a mechanism for operably interfacing with the pump so as to enable the pump to pump fluid through the applicator module.

34. The module of claim 33 wherein the cassette comprises a heat exchange element.

35. The module of claim 34 wherein said module contains a fluid.

36. The module of claim 34 wherein the pad further comprises:
a. a covering for the pad; and
b. means for reversibly affixing the covering to the pad in a manner such that the covering may be removed from the pad.

37. The module of claim 34 wherein the pad is reusable.

38. The module of claim 34 wherein the pad is disposable.

* * * * *